United States Patent
Kersken et al.

(10) Patent No.: US 10,321,897 B2
(45) Date of Patent: Jun. 18, 2019

(54) OVULATION DETERMINATION

(71) Applicant: VivoSensMedical GmbH, Leipzig (DE)

(72) Inventors: Tim Kersken, Leipzig (DE); Henry Alexander, Leipzig (DE)

(73) Assignee: VivoSensMedical GmbH, Leipzig (DE)

( * ) Notice: Subject to any disclaimer, the term of this patent is extended or adjusted under 35 U.S.C. 154(b) by 391 days.

(21) Appl. No.: 15/024,523

(22) PCT Filed: Sep. 26, 2014

(86) PCT No.: PCT/EP2014/070710
§ 371 (c)(1),
(2) Date: Mar. 24, 2016

(87) PCT Pub. No.: WO2015/044398
PCT Pub. Date: Apr. 2, 2015

(65) Prior Publication Data
US 2016/0270768 A1 Sep. 22, 2016

(30) Foreign Application Priority Data
Sep. 26, 2014 (GB) .................................. 1317149.1

(51) Int. Cl.
*A61B 5/00* (2006.01)
*A61B 10/00* (2006.01)
*A61B 5/01* (2006.01)

(52) U.S. Cl.
CPC ............ *A61B 10/0012* (2013.01); *A61B 5/01* (2013.01); *A61B 5/6847* (2013.01); *A61B 2010/0019* (2013.01)

(58) Field of Classification Search
None
See application file for complete search history.

(56) References Cited

U.S. PATENT DOCUMENTS

| 4,151,831 A | 5/1979 | Lester |
| 8,496,597 B2 * | 7/2013 | James ............... A61B 10/0012 600/551 |
| 2012/0016258 A1 | 1/2012 | Webster et al. |

(Continued)

FOREIGN PATENT DOCUMENTS

WO 2008/029130 A2 3/2008

OTHER PUBLICATIONS

International Search Report and Written Opinion in corresponding International Application No. PCT/EP2014/070710, dated Jan. 1, 2015.

(Continued)

*Primary Examiner* — Max F Hindenburg
(74) *Attorney, Agent, or Firm* — J.A. Lindeman & Co. PLLC; Joseph Parisi; Jeffrey Lindeman

(57) ABSTRACT

The present disclosure relates to a method and a system for determining the fertility status of a female. The method comprises the steps of determining and recording a continuous series of temperature data points relating to a body temperature of the female, identifying if the series of temperature data points comprises at least one pre-determined feature in the series of temperature data points and, if a pre-determined feature has been identified, determining a point in time of ovulation for the series of temperatures based on a pre-determined relation of the pre-determined feature and ovulation.

11 Claims, 7 Drawing Sheets

(56) References Cited

U.S. PATENT DOCUMENTS

2013/0137940 A1    5/2013  Schafer
2013/0237771 A1*   9/2013  Runkewitz ......... A61B 10/0012
                                                        600/301

OTHER PUBLICATIONS

International Preliminary Report on Patentability in corresponding International Application No. PCT/EP2014/070710, dated Mar. 29, 2016.

* cited by examiner

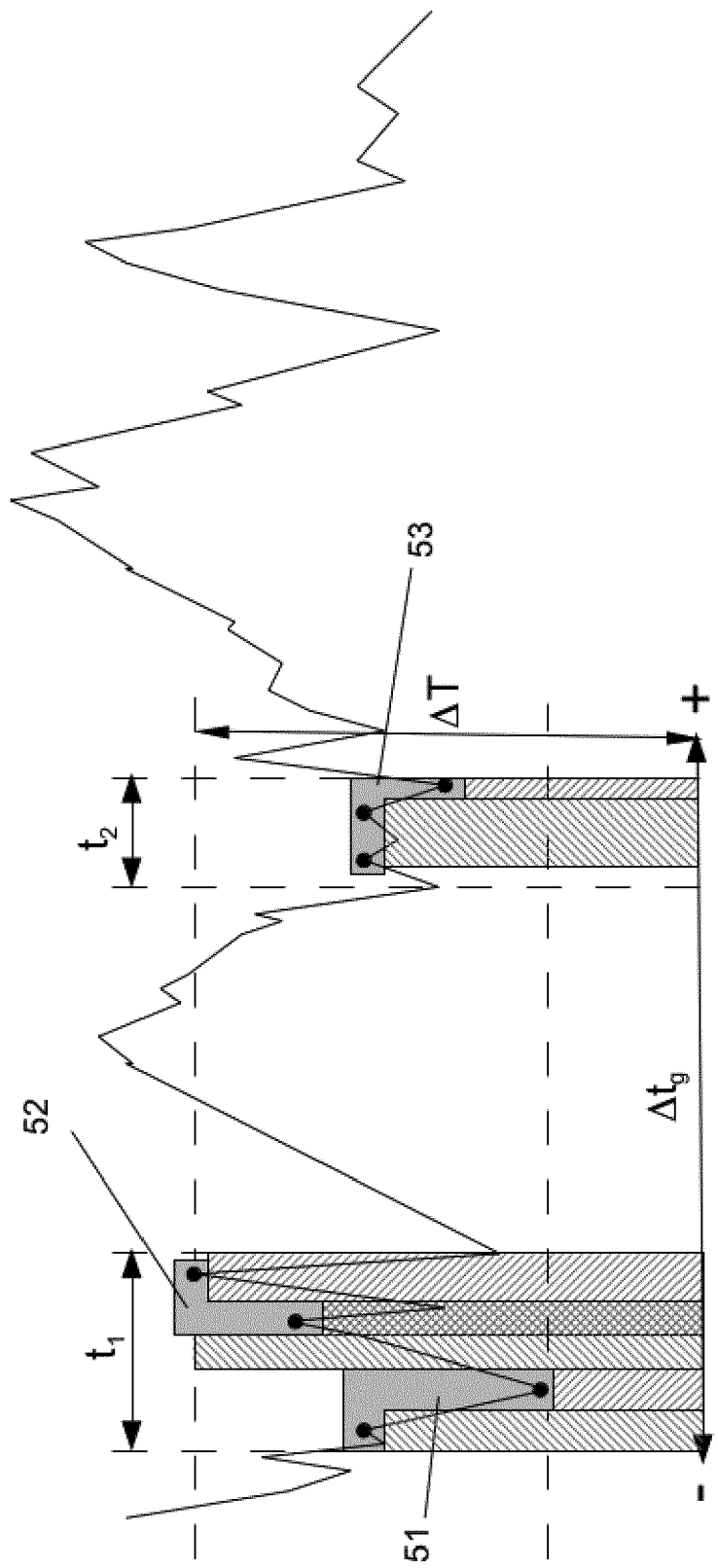

OVULATION DETERMINATION

CROSS REFERENCE TO RELATED APPLICATION

The present application claims priority to GB 131 71 49.1, filed on 26 Sep. 2013, the entire content of which is incorporated by reference herewith.

FIELD OF THE INVENTION

The present invention relates to a method and a system for determining the fertility status of a female based on body temperatures.

INTRODUCTION

Fertility is one of the most important health care aspects in the society. Fertility and fecundity are associated with several factors such as psychological, environmental and chemical factors. The increasing influence of environmental factors and knowledge about the associated risks to such factors are leading to a growing need for methods by which the fertility of the population can be assessed without significant encroachment of the personal circumstances of test persons. The lack of available methods for fertility screening for women is discussed in Reproduction Toxicology (1990), Vol. 4, Pages 1-2. Measurement methods for the evaluation of the menstrual cycle and fertility of women are much needed that will not encroach on their daily routines.

Determining fertility either for family planning or for contraception is a critical approach of the female health care system and precise determination of ovulation is required. So far, some indirect methods to determine the ovulation in women are based on serum hormone levels or measurement of the basal body temperature. The method using serum hormone levels is reliable but the wide employment of laboratory diagnostic methods that are required for these measurements in urine leads to substantial costs. Otherwise, a postovulatory rise in the temperature of about 0.5° C. (+/−0.1° C.) has been documented in the evaluation of the course of the menstrual cycle. This temperature rise is due to the circadian variations of the body core temperature amount to ±0.5° C.

Conventional methods are based on the estimation of a basal temperature, the lowest temperature during a day. This usually is in the morning after wake up and involves an inconvenient temperature measurement right after waking up. A change in this basal temperature is used as an indication for ovulation. This method is not very reliable.

There is a need to provide a reliable forecast for ovulation in a female and to determine the actual fertility status of the woman or female.

SUMMARY OF THE INVENTION

The present disclosure suggests a method and a system for determining the fertility status of a female as outlined in the independent claims. Optional additional features are presented in the dependent claims.

In one aspect, the method comprises the steps of determining and recording a continuous series of temperature data points relating to a body temperature of the female, identifying if the series of temperature data points comprises at least one pre-determined feature in the series of temperature data points and, if a pre-determined feature has been identified, determining a point in time of ovulation for the series of temperatures based on a pre-determined relation of the pre-determined feature and ovulation.

In another alternative or additional aspect, the method comprises the steps of determining and recording a plurality of temperature curves over a menstrual cycle of the female, the temperature curve relating to a body temperature of the female, analysing the homogeneity of each one of the plurality of temperature curves and determining if the homogeneity has a break, determining a point in time of the break in the menstrual cycle of the female, and estimating a point of time of ovulation in the menstrual cycle of the female and out-putting the estimated point of time of ovulation.

In another aspect, the system comprises a temperature measurement device for determining and recording a series of temperature data points relating to a body temperature of the female and an analysing tool for analysing the series of temperature date points. The series of temperature data points a transferred from the temperature measurement device to the analysing tool. The analysing tool performs the steps of identifying if the series of temperature data points comprises at least one pre-determined feature in the series of temperature data points and, if a pre-determined feature has been identified, determining a point in time of ovulation for the series of temperature data points based on a pre-determined relation of the pre-determined feature and ovulation.

In yet another aspect, the analysing tool performs the steps of analysing the homogeneity of each one of the plurality of temperature curves and determining if the homogeneity has a break, determining a point in time of the break in the menstrual cycle of the female, and estimating a point of time of ovulation in the menstrual cycle of the female and out-putting the estimated point of time of ovulation.

The methods and systems of the present disclosure improve prognosis of ovulation ant thus the termination of the fertility status of the female.

DESCRIPTION OF THE FIGURES

The invention may be better understood when reading the detailed description of examples of the present disclosure which is given with respect to the accompanying figures in which:

FIG. 5 shows examples of features that may be used with pattern or feature analysis;

DETAILED DESCRIPTION

Examples of the present disclosure will now be described in more detail. It is to be understood that the described examples and the examples shown in the figures are purely illustrative and a person skilled in the art will amend the examples according to specific requirements. It is not necessary to implement all features shown in the examples and a person skilled in the art will combine features shown or described with respect to one figure with examples shown in other figures or described elsewhere in the present disclosure.

Determining fertility either for family planning or for contraception is a critical approach of the female health care system and precise determination of ovulation is required. The present disclosure seeks to provide a woman a prognosis of the "fertility window" when the ovulation may occur.

The present disclosure relates to a method and a system for determining a fertility status of a female by measuring a body core temperature and for determining a prognosis for ovulation.

Figure 1:
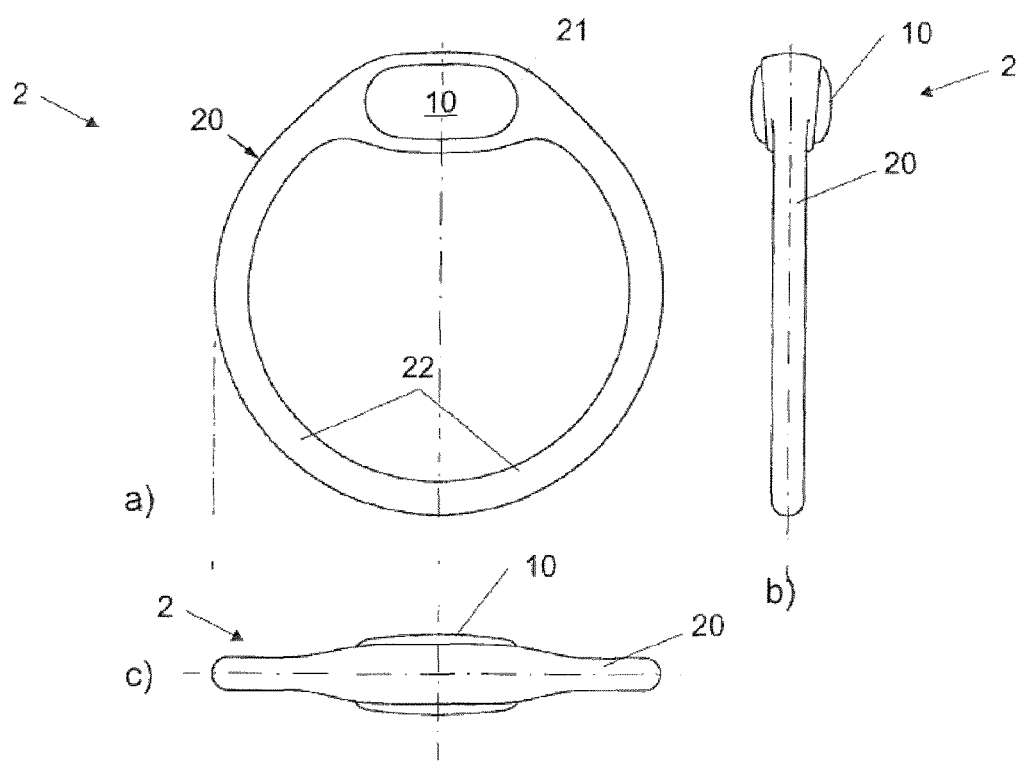
FIG. 1 shows a pessary that may be used with the present disclosure

The present invention provides a method for determining the fertility status of the female by using data determined by a temperature sensor placed in the vaginal channel of the female. An example of a temperature sensor that may be used with the present disclosure is shown in FIGS. 1a to 1c and described in US 2013/0237771 (EP 2567680), the content of which is incorporated herein by reference. The temperature sensor 10 may have the form of a pessary or may be attached to a pessary 20 placed in the vaginal channel of the female. The temperature sensor 10 can measure the actual temperature of the body core of the user inside the vaginal channel. The measured temperatures may therefore be termed body core temperature. The temperature sensor is able to measure and record circamensual (30 days and more) a series of body core temperature data points.

The body core temperature is the most reliable temperature measurement of a human or animal and is by far more precise than measurements on other places, where they are often influenced by external or environmental conditions.

Figure 2A:
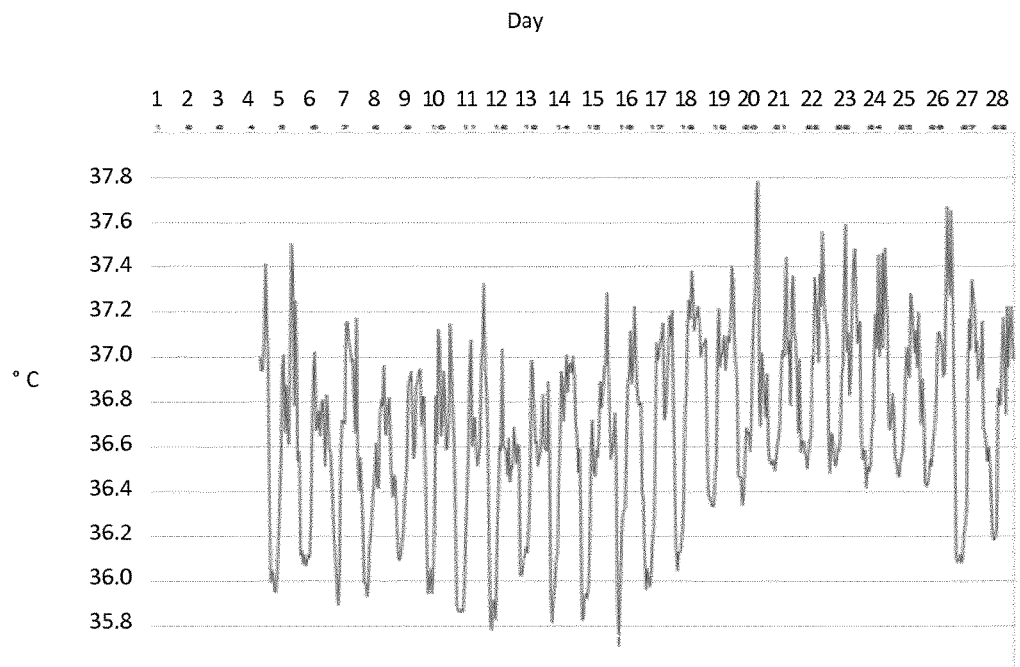
FIGS. 2a and 2b show examples of temperature curves that may be determined with the analysing system of FIG. 1.
Figure 2B:
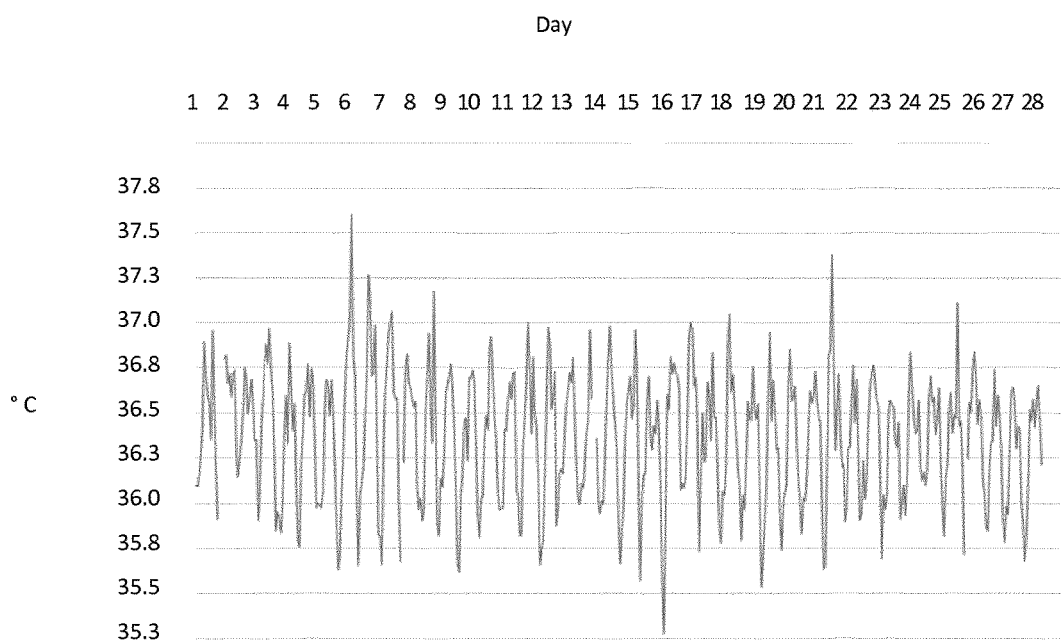

The series of body core temperature data points may be determined continuously, for example every 5 minutes over 24 hours a day, 7 days a week resulting in about 288 temperature data points per day. The time interval may be greater or less than five minutes, for example every minute or every 10 or 15 minutes resulting in more or less temperature data points per day. It is advantageous, however, to monitor the temperature continuously over the whole day, during night and day, and if possible over the entire menstrual cycle of the female. A continuous temperature data curve can be evaluated from these temperature data points representing the actual body core temperature of the female. Examples for continuous temperature data curves are shown in FIGS. 2a and 2b, where 288 temperature data points per day were measured and recorded continuously every 5 minutes over a menstrual cycle (about 30 days or more).

Conventional approaches, for example, measure the temperature data only during sleep phases, i.e. during the nights and the temperature sensor is removed for read out in the morning. These approaches try to estimate a basal temperature based on the lowest temperatures measured during the sleep phase. Other conventional approaches involve a measurement right after waking up. These methods aim to determine a basal temperature which is often not well defined and the method is not very reliable. In addition, these methods are also influenced by the behaviour and the conditions of the user. Not every night and sleep phase is the same and variations in the life style, the amount and time of sleep may have a strong influence on the measured values.

The present disclosure suggest the use of a continuous series of temperature data points of the body core temperature measured in the vaginal channel of the female which are determined and recorded continuously over days, weeks or circamensual to determine temperature curves of the body core temperature over long periods. Depending on the application, the sensor may remain in the vagina for the entire menstrual cycle and the recorded data may be read out at the end of the menstrual cycle. Alternatively, the recorded temperature data may be read out regularly, for example once or twice a day. The measurement and read-out of the actual temperature data makes an "real-time" prediction of ovulation possible.

These recorded temperature curves may be analysed and/or evaluated to determine a prognosis or prediction of future ovulation. It is to be understood that a prediction of a point in time of ovulation is given by probabilities for ovulation. There are different methods that can be applied to determine probabilities and to predict ovulation and/or a fertility window from one or more series of temperature data point and/or from temperature curve recorded over one or more menstrual cycles. Different methods are outlined below. One or more of these methods may be combined to enhance the reliability of the prediction.

Homogeneity Analysis

Figure 3:
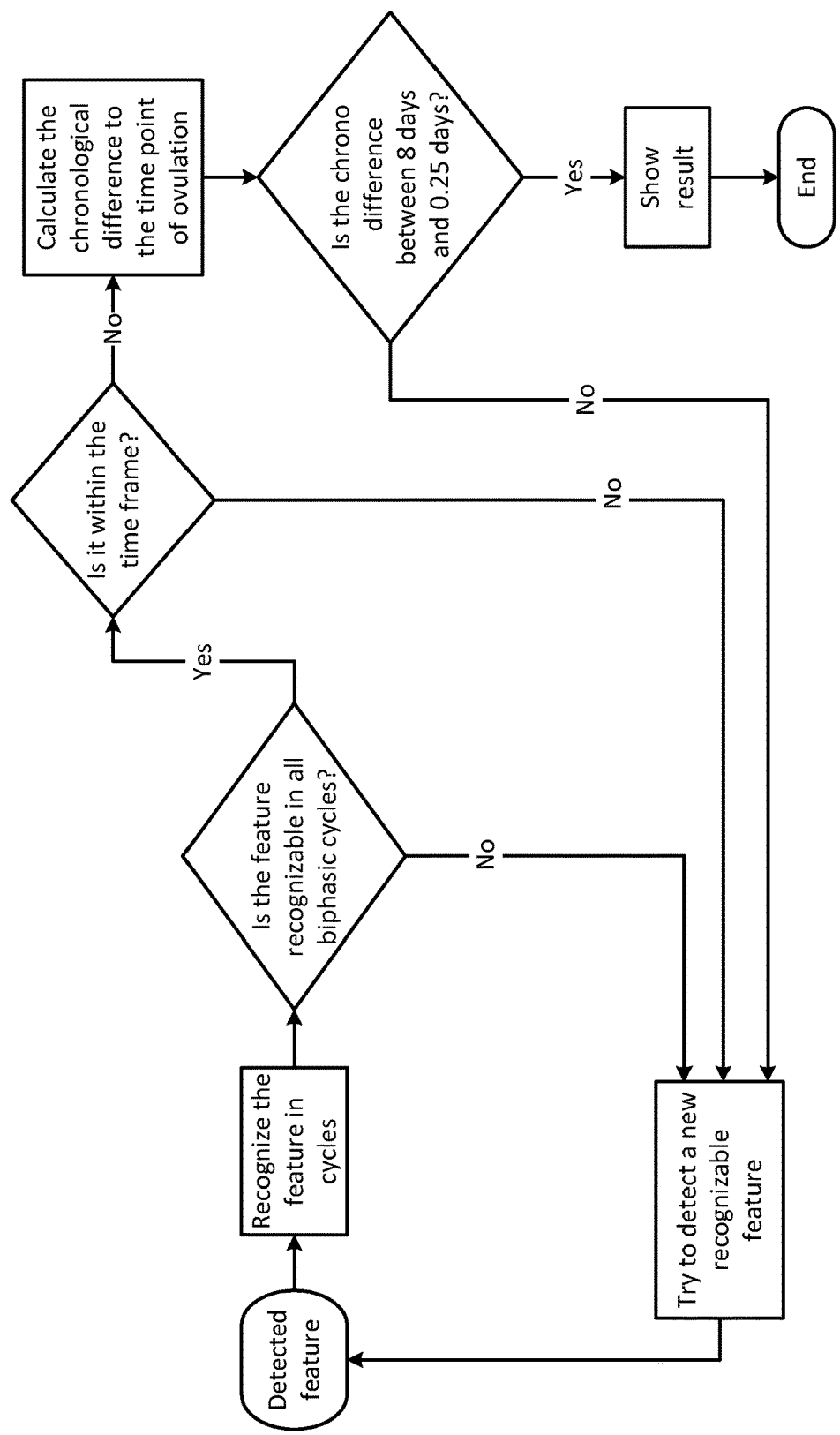
FIG. 3 illustrates a method for determining the point of ovulation based on homogeneity analysis.

A temperature curve of a menstrual cycle may be analysed after the measurement of the entire menstrual cycle has been recorded. The temperature curve or the individual temperature data points of this menstrual cycle may be analysed for homogeneity. An example for a method for analysing homogeneity is illustrated in FIG. 3.

A menstrual cycle can be classified as bi-phasic or as mono-phasic cycle depending on whether a break in the homogeneity of the temperature curve can be found. The break separates the temperature curve of a bi-phasic cycle in a first cycle phase, termed luteal phase before the break and a second cycle phase, termed follicular phase after the break. A break in homogeneity can be defined as a break in the measured temperature curve of at least 0.2° Celsius. If this break in temperature is positive, i.e. the break involves an increase in temperature and if the second cycle phase lasts for at least ten days or more, the cycle may be considered as bi-phasic. If the second phase after a break is less than ten days and/or if the break is negative, i.e. involves a decrease in temperature, or less than about 0.2° Celsius, the cycle may be considered as mono-phasic.

Figure 4A:
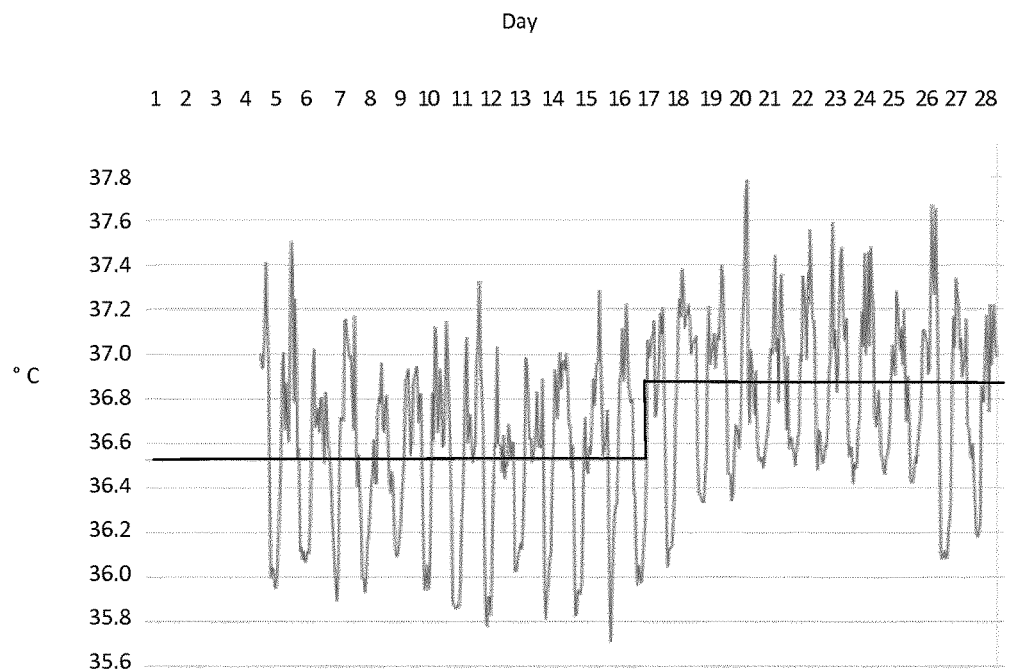
FIGS. 4a and 4b show the temperature curves of FIGS. 2a and 2b, with and without analysed break, respectively.

FIG. 4a shows the temperature curve of FIG. 2a, analysed for homogeneity. A break in homogeneity with an increase of temperature of more than 0.3° C. and with the second phase extending over 12 days could be found. This temperature curve has been determined as bi-phasic.

Figure 4B:
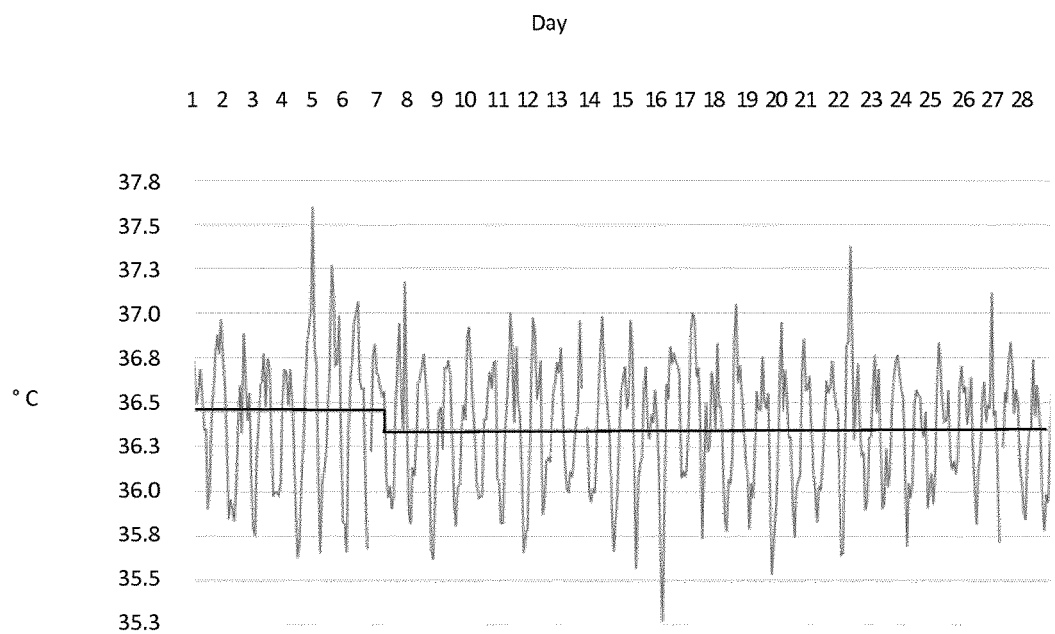

FIG. 4b shows the temperature curve of FIG. 2b, analysed for homogeneity. A negative break towards lower temperatures was determined with a delta of less than 0.2° C. This break does not meet criteria for a break in homogeneity. This cycle is therefore considered as mono-phasic.

The point in time of ovulation is considered to be 24 hours before the break. If three or more menstrual cycles of the same female are determined as bi-phasic, they may be classified by the increase in temperature, length of the cycle, length of the luteal phase and length of the follicular phase. Based on these data, a probability for ovulation on every day of the cycle can be calculated for this female. This information may be presented or output to a user on a display, such as a screen of computer, or other electronic device. The output may comprise the day of the menstrual cycle with the highest probability of ovulation and the days before or after this day with still high probability for ovulation. For example, the day with the highest probability of ovulation is output, and five days before and three days after that day, if for each of these day, the probability is above a predetermined value. This can depend on the variance of the determined break in the acquired temperature curves. This determination can be used as a prediction for the ovulation and/or a fertility window of the next menstrual cycle of that female.

The above prognosis or prediction based on homogeneity test may be used alone or in combination with the method described below. Combining the above homogeneity based prognosis with a pattern based determination of ovulation described below may lead to an increase in reliability of the determination of ovulation at a point in time before the actual ovulation occurs.

Pattern Analysis

Pattern analysis may be used for determination or prediction of ovulation in the present menstrual cycle of the female. In this application, the temperature data points are measured, recorded and read out during the menstrual cycle. The reader may be connected to a computer and the temperature data points may be analysed and evaluated with a computer program running on this computer. It is also possible to use an internet based analysis tool and to transfer the temperature data points via the internet to the analysis tool either directly from the reader or via an internet access device, such as a computer, smartphone tablet or the like.

A time series of temperature data points can be read out and evaluated at any time during the menstrual cycle. For example, the temperature data points may be read out or transmitted to a reader or analysis device once every 24 hours or twice a day. The temperature curve corresponds then to the present menstrual cycle of the female up to the last temperature measurement before read-out, i.e. before the pessary was removed from the vagina. The time series of temperature data points is thus in this case not a complete menstrual cycle but only a first portion. A prediction of ovulation can be made in real-time during the menstrual cycle.

The time series of temperature data points may now be analysed for pre-determined features or patterns. Principles of pattern analysis have been described in mathematical theories. The present disclosure suggests the use of such a pattern analysis for analysing temperature curves of body core temperatures in a female.

Figure 6:
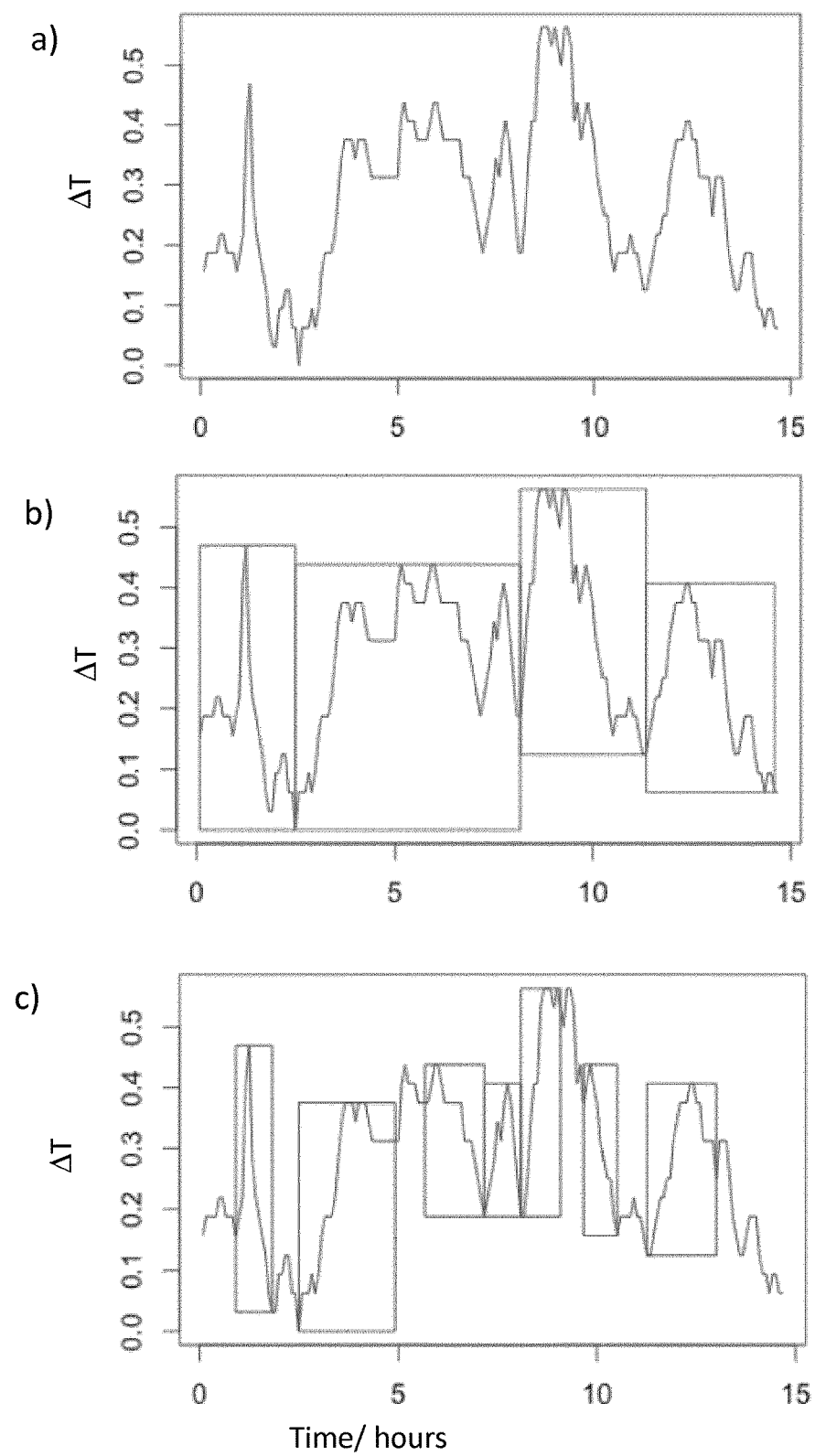
FIG. 6 shows further examples of a pattern analysis.

FIGS. 5 and 6 show sections of two temperature curves taken from a series of temperature data point in which patterns are identified. These examples are purely illustrative and by no means intended to a specific pattern. Every series of data points may be different and different shapes and types of features or patterns may be identified as relevant for ovulation.

Example 1

FIG. 5 shows a first example of features or pattern analsysed in a section or subset of a series or temperature data points taken from a woman. The pre-determined feature or pattern may be an increase or a decrease in temperature or a certain sequence of peaks as illustrated by patterns 51, 52, and 53 in FIG. 5. For example, a first feature 51 may be a decrease in temperature followed by a second feature 52 of two subsequent peaks at a higher temperature value than the first feature 51. A pre-determined feature may be each one of the first feature or second feature separately or a combination of the first feature 51 and the second feature, for example within a time interval t1. The pre-determined feature or pattern may also be the combination of the first feature 51 and the second feature 52 with a third feature 53 that all occur within a time interval Δtg. An alternative or additional requirement may be that the third feature is found within a time interval t2 and/or at a certain temperature.

These and/or other features can be combined to determine and define the pre-determined feature.

The pre-determined pattern or feature may more generally relate to an increase, a decrease, specific peak temperatures, temperature difference, time intervals, peak frequencies and any combination thereof.

The pre-determined feature or pattern may be a pattern identified in previous cycles of the same female or may be a pattern present in the menstrual cycle of a specific group or of all females or any combination thereof. For example, a feature may be considered, if it has been observed in about 70% or more of all considered bi-phasic cycles of all users detected and analysed with the present method.

Example 2

FIG. 6 shows another example of a section of a temperature curve in which a pattern is analysed by pattern recognition. In a first step, a measured series of temperature data points may be subdivided in a plurality of subsets of the temperature data points. Each subset of temperature data points may correspond to a day in the menstrual cycle but other time intervals can be used as well. A specific indicator, termed PuK-indicator, may be determined for each subset of temperature data points. Based on the PuK indicator, each subset of the temperature data points may be assigned to a first phase before ovulation (L1-phase) or a second phase after ovulation (L2 phase) in the menstrual cycle. Other additional phases may be added if considered necessary. In addition to the PuK indicatort, the temperature median of the subset of temperature data points may be used for the assignment of the subset of temperature data points the first phase before ovulation (L1-phase) or to the second phase after ovulation (L2 phase).

The PuK indicator is an indicator for temperature stress and may also be termed temperature-stress-indicator. An example of the determination of the PuK-indicator is shown with respect to a single subset of temperature data points in FIG. 6. FIG. 6a shows the subset of temperature data points in a temperature curve as measured for example with the temperature sensor described with respect to FIG. 1. Temperature measurements were taken every 5 minutes in this example.

The PuK-indicator determines and evaluates in this example the peaks of the respective subset of temperature data points. The peaks are usually irregular and can not be determined or predicted in any way. Furthermore, the number of peaks depends on different situations, for example peaks can be caused by sports activities, every day activities, diseases or hormones to give just a few examples. The present example aims to identify and analyse peaks or patterns of peaks caused by hormones or hormonal changes. The female body emits high numbers of the hormone progesterone prior to ovulation which has an influence on the body temperature, as known in the art. Peaks caused by hormones can be determined with a certain probability by evaluating based on the length, intensity and frequency of peaks which can be termed a feature of temperature curve or the PuK- or temperature-stress indicator.

To analyse the feature or pattern of a subset of temperature data points as illustrated in FIG. 6a, first, peaks have to be identified. Identification of a peak may vary for different persons or different time scales. In some cases peaks can be easily recognized, while other peaks may be more difficult to determine, for example if two or more peaks are very close together or if temperature variation is very little.

Identified peaks can then be classified as "wide" peaks shown within the squares in FIG. 6b and "acute" peaks shown in square in FIG. 6c. A peak may be classified as "wide" peak if the peak has, for example, a certain length, magnitude or slope, or any combination thereof. Peak criteria for acute peaks may be identified by at least one peak characteristics that may be selected from magnitude, slope or length, wherein the length is shorter than the length of a wide peak. Known mathematical method for pattern analysis can be used for the determination and for the adaption of the peak. A high number and/or a high frequency of acute peaks may be an indicator for high temperature stress.

The pattern of the acute peaks and/or the pattern of the wide peaks may be considered a feature of the series or subset of the series of temperature data points. The pattern of the acute peaks and/or the pattern of the wide peaks may be compared to data base patterns that may be recorded from the same women and the corresponding subset of the series of data points may be classified as belonging to phase L1 or phase L2. In this way, each subset of the series of data point can be classified. If the subset corresponds for example to the day at which the analysis is made, a real time estimation can be given, if the woman is in phase L1 or L2. Thus every day of the menstrual cycle can be classified as belonging to phase L1 or phase L2.

The method has been tested and showed with more than 94% reliability the correct phase of the menstrual cycle.

The example above determines the PuK indicator based on the peaks in the series of temperature data points. Alternative examples may use other characteristics of the data points such as minima, slope or other features of the series of temperature data points.

All examples shown above may be further improved by a cycle start and/or a cycle end determination. This cycle start determination determines based on the series of temperature data points the start of the menstrual cycle. This can make the determination of ovulation more precise and improves prediction quality when the woman has strongly varying and/or long menstrual cycles.

The temperature curves may be used as biomarker for hormone events. This is based on the finding that hormone levels have an influence on the body core temperature. The luteinizing hormone (LH) or other hormones such as estradiol and progesterone that effect the implantation of an embryo in the uterus have an direct or indirect influence on the body temperature. This effect is sometimes termed thermal depressive effect. However, there is not direct correlation between the hormone level and the temperature curve and the temperature cure itself does not correspond to ore represent the hormone level. The present disclosure suggests a method and a system for monitoring the body core temperature in real-time which enables to detect changed in the hormone levels in real time.

Figure 7:
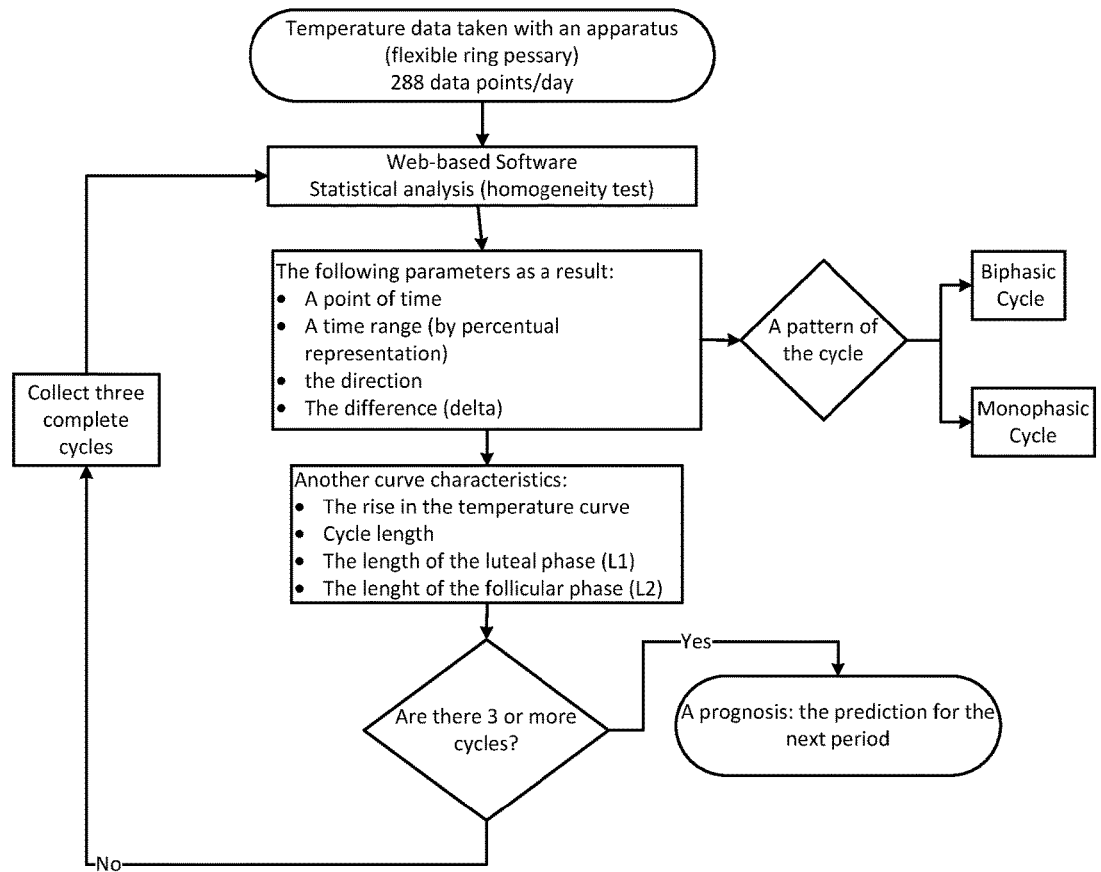
FIG. 7 illustrates a method for determining the point of ovulation based on pattern analysis.

FIG. 7 illustrates and example of how ovulation of the fertility window may be predicted. If the pre-determined pattern or feature is identified in the present series of temperature data points, it is verified that the feature was measured in the expected time window. If the time window is accepted, a relation of the feature to the point of time of ovulation is made and a prognosis for ovulation can be given. For example, if the feature occurs 48 hours before ovulation, a prediction of ovulation can be calculated for a point in time 48 hours after the occurrence of the feature in the time series of temperature data points. In this way, it is possible to make a prediction of ovulation based on the actual menstrual cycle of the female.

It is also possible, to combine the prediction based in pattern analysis with the homogeneity method described above. In this case the probability of ovulation may be increased or decreased depending on whether both methods predict the same or a similar time of ovulation or of a fertility window or if they are contradicting.

The above disclosure has been given with respect to the determination of the fertility status of a human female. The method and the system, however, are equally applicable with any mammalian female where a continuous temperature measurement is possible.

The invention claimed is:

1. A method of using a temperature sensor and a reader device for determining the fertility status of a female, the method comprising:
   generating with the temperature sensor a continuous series of temperature data points relating to a body temperature of the female during night and day and continuously over a plurality of days, wherein the continuous series of temperature data points is continuously recorded in a memory device;
   transmitting the recorded continuous series of temperature data points from the memory device to the reader device;
   analysing the continuous series of temperature data points on the reader device, wherein the analysing comprises comparing the continuous series of temperature data points to pattern analysis criteria to determine a pattern of temperature data points in the continuous series of temperature data points;
   identifying if the continuous series of temperature data points comprises a pattern indicative of at least one pre-determined feature in the continuous series of temperature data points based on the comparison of the continuous series of temperature data points to pattern analysis criteria; and
   if a pattern indicative of a pre-determined feature has been identified, determining a point in time of ovulation for the continuous series of temperatures based on a pre-determined relation of the pre-determined feature and ovulation, wherein the pre-determined feature comprises at least one of a temperature-stress-indicator, a number of peaks, a sequence of peaks, a combination of at least one of increases and decreases of temperatures, or any combination thereof within a first time interval.

2. The method of claim 1, wherein the body temperature is a body core temperature measured in the vaginal channel of the female and the continuous series of temperature data points relate to the body core temperature.

3. The method of claim 1, wherein the determining and recording the continuous series of temperature data points comprises measuring a temperature data in intervals of every 10 minutes or less and storing data relating to the temperature value in a memory.

4. The method of claim 3, wherein the determining and recording the continuous series of temperature data points comprises measuring the temperature data in intervals of every 10 minutes or less continuously over at least 24 hours.

5. The method of claim 1, wherein the determining and recording the series of temperature data points comprises measuring temperature data with a temperature sensor and a data memory in a pessary placed in the vaginal channel of the female.

6. The method of claim 1, wherein the pre-determined feature is present in a plurality of previously recorded menstrual cycles of the female.

7. The method of claim 1, wherein the pre-determined feature is present in a plurality menstrual cycles of a plurality of females.

8. The method of claim 1, wherein the pre-determined feature is present in a follicular phase of a plurality of menstrual cycles.

9. The method of claim 1, further comprising:
   determining a homogeneity of a plurality of temperature curves and determining if the homogeneity has a break in the homogeneity,
   if a break in the homogeneity has been determined, identifying a probability for ovulation and determining how the probability for ovulation corresponds to the determined point in time of ovulation.

10. The method of claim 9, wherein the plurality of temperature curves is recorded from the female.

11. A method of using a temperature sensor and a reader device for determining the fertility status of a female, the method comprising:
   Generating with the temperature sensor a continuous series of temperature data points relating to a body temperature of the female during night and day and continuously over a plurality of days, wherein the continuous series of temperature data points is continuously recorded in a memory device;
   transmitting the recorded continuous series of temperature data points from the memory device to the reader device;
   analysing the continuous series of temperature data points on the reader device, wherein the analysing comprises comparing the continuous series of temperature data points to pattern analysis criteria to determine a pattern of temperature data points in the continuous series of temperature data points;
   identifying if the continuous series of temperature data points comprises a pattern indicative of at least one pre-determined feature in the continuous series of temperature data points based on the comparison of the continuous series of temperature data points to pattern analysis criteria; and
   if a pattern indicative of a pre-determined feature has been identified, determining a point in time of ovulation for the continuous series of temperatures based on a pre-determined relation of the pre-determined feature and ovulation, wherein the pre-determined feature is based on relative changes in the series of temperature data points that are a biomarker representing a change in the fertility status.

* * * * *